US00PP34417P2

(12) United States Plant Patent
Yamada

(10) Patent No.: US PP34,417 P2
(45) Date of Patent: Jul. 12, 2022

(54) ***MANDEVILLA* PLANT NAMED 'SUNPA 0931'**

(50) Latin Name: *Mandevilla hybrida*
Varietal Denomination: 'Sunpa 0931'

(71) Applicant: Masahiro Yamada, Shiga (JP)

(72) Inventor: Masahiro Yamada, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 17/571,473

(22) Filed: Jan. 8, 2022

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Mandevilla* plant named 'Sunpa 0931', characterized by its upright to outwardly spreading plant habit; vigorous growth habit; freely branching habit; early and freely flowering habit; long flowering period; and medium-sized yellow-colored flowers with orange-colored centers.

1 Drawing Sheet

Figure 1:
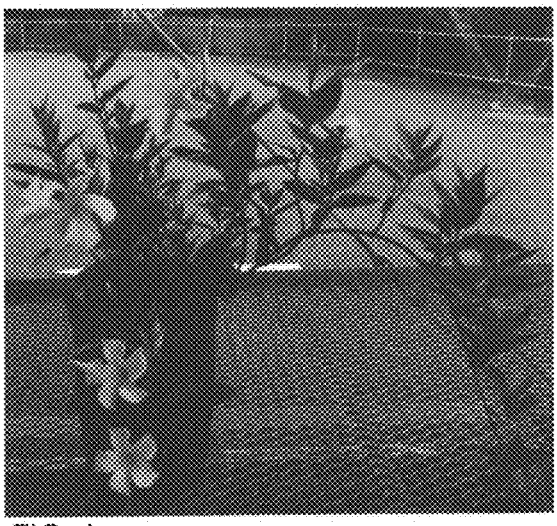

Botanical designation: *Mandevilla hybrida.*
Cultivar denomination: 'SUNPA 0931'.

STATEMENT REGARDING PRIOR DISCLOSURES BY THE INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla hybrida* and hereinafter referred to by the name 'Sunpa 0931'.

The new *Mandevilla* plant is a product of a planned breeding program conducted by the Inventor in Higashiomi, Shiga, Japan. The objective of the breeding program is to create new upright and freely branching *Mandevilla* plants with freely flowering habit and attractive flowers.

The new *Mandevilla* plant originated from a cross-pollination conducted by the Inventor in Higashiomi, Shiga, Japan in May, 2015 of a proprietary selection of *Mandevilla hybrida* identified as code number 13M267-1, not patented, as the female, or seed parent with a proprietary selection of *Mandevilla hybrida* identified as code number 13M274-1, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in September, 2016.

Asexual reproduction of the new *Mandevilla* plant by terminal vegetative cuttings in Higashiomi, Shiga, Japan since March, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 0931'. These characteristics in combination distinguish 'Sunpa 0931' as a new and distinct *Mandevilla* plant:

1. Upright to outwardly spreading plant habit.
2. Vigorous growth habit.
3. Freely branching habit.
4. Early and freely flowering habit.
5. Long flowering period.
6. Medium-sized yellow-colored flowers with orange-colored centers.

Plants of the new *Mandevilla* can be compared to plants of the female parent selection. Plants of the new *Mandevilla* differ primarily from plants of the female parent selection in flower color as plants of the new *Mandevilla* have darker yellow-colored flowers than plants of the female parent selection. In addition, plants of the new *Mandevilla* have larger flowers than plants of the female parent selection.

Plants of the new *Mandevilla* can be compared to plants of the male parent selection. Plants of the new *Mandevilla* differ primarily from plants of the male parent selection in flower color as plants of the new *Mandevilla* have brighter yellow-colored flowers than plants of the male parent selection. In addition, plants of the new *Mandevilla* have larger flowers than plants of the male parent selection.

Plants of the new *Mandevilla* can be compared to plants of the *Mandevilla hybrida* 'Sunpa 2671', disclosed in U.S. Plant Pat. No. 31,661. In side-by-side comparisons, plants of the new *Mandevilla* differ from plants of 'Sunpa 2671' in the following characteristics:

1. Plants of the new *Mandevilla* have shorter internodes than plants of 'Sunpa 2671'.
2. Leaves of plants of the new *Mandevilla* are decussate whereas leaves of plants of 'Sunpa 2671' are opposite.
3. Leaves and leaf petioles of plants of the new *Mandevilla* are darker green in color than leaves and leaf petioles of plants of 'Sunpa 2671'.
4. Petals of plants of the new *Mandevilla* are not imbricate whereas petals of plants of 'Sunpa 2671' are imbricate.
5. Plants of the new *Mandevilla* have shorter peduncles than plants of 'Sunpa 2671'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet (FIG. 1) is a side perspective view of a typical flowering plant of 'Sunpa 0931' grown in a container.

Figure 2:
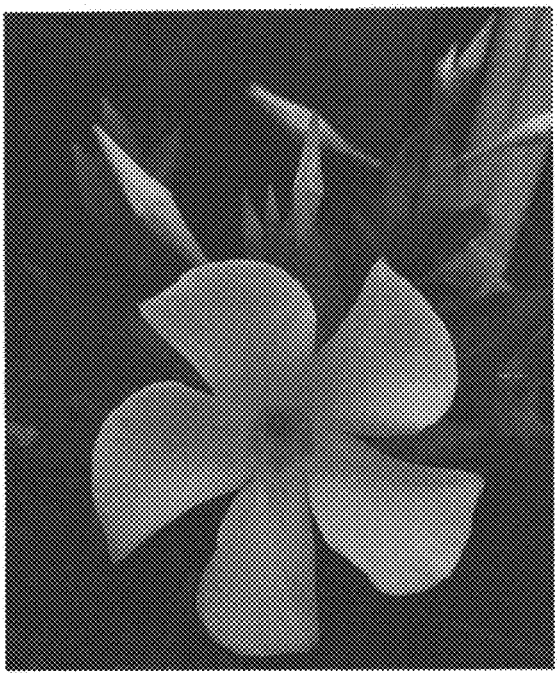

The photograph at the bottom of the sheet (FIG. 2) is a close-up view of a typical flower of 'Sunpa 0931'.

DETAILED BOTANICAL DESCRIPTION

The aforementioned photographs and following observations, measurements and values describe plants grown during the late summer in 18-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 0931'.

Parentage:

*Female, or seed, parent.*—Proprietary selection of *Mandevilla hybrida* identified as code number 13M267-1, not patented.

*Male, or pollen, parent.*—Proprietary selection of *Mandevilla hybrida* identified as code number 13M274-1, not patented.

Propagation:

*Type.*—By terminal vegetative cuttings.

*Time to initiate roots, summer and winter.*—About two weeks at temperatures about 23° C. to 25° C.

*Time to produce a rooted young plant, summer and winter.*—About five to six weeks at temperatures about 23° C. to 25° C.

*Root description.*—Fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading plant habit; vigorous growth habit; freely branching habit with about six primary lateral branches; suitable for hanging baskets and garden plantings.

*Plant height.*—About 35 cm.

*Plant diameter.*—About 50 cm.

*Lateral branch description.*—Length: About 20.6 cm. Diameter: About 2.8 mm. Internode length: About 1.3 cm. Strength: Strong, flexible. Texture: Smooth, glabrous. Color, developing: Close to 138A. Color, fully developed: Darker green than 148A.

Leaf description:

*Arrangement and quantity.*—Decussate, simple; about 20 leaves per lateral branch.

*Length.*—About 7 cm.

*Width.*—About 3.1 cm.

*Shape.*—Oblong.

*Apex.*—Acuminate.

*Base.*—Cordate.

*Margin.*—Entire; not undulate to slightly undulate.

*Texture and luster, upper and lower surfaces.*—Smooth, glabrous; glossy.

*Venation pattern.*—Pinnate, reticulate.

*Color.*—Developing leaves, upper surface: Close to 144A. Developing leaves, lower surface: Close to 146C. Fully expanded leaves, upper surface: Close to NN137A; venation, close to NN137C. Fully expanded leaves, lower surface: Close to 138A; venation, close to 137D.

*Petioles.*—Length: About 8 mm. Diameter: About 1.7 mm. Texture, upper and lower surfaces: Smooth, glabrous. Color, upper and lower surfaces: Close to 146A.

Flower description:

*Flower type and habit.*—Single salverform flowers; flowers face upright to outwardly; freely flowering habit with about four to six flowers per axil and about 42 flowers developing per plant.

*Natural flowering season.*—Early flowering habit, plants begin flowering about six weeks after planting rooted cuttings; long flowering period, plants flower continuously from summer until late autumn in Japan.

*Flower longevity on the plant.*—About seven to ten days; flowers not persistent.

*Fragrance.*—None detected.

*Flower buds.*—Height: About 5 cm. Diameter: About 9.7 mm. Shape: Rhombic. Color: Proximally, close to 149C and distally, close to 8B and 40C.

*Flowers.*—Appearance: Salverform; flared trumpet, corolla fused and five-parted; flowers roughly star-shaped. Diameter: About 6.9 cm. Depth (length): About 3.5 cm. Throat diameter: About 1.1 cm. Tube length: About 1.3 cm. Tube diameter, proximally: About 2.8 mm.

*Corolla.*—Quantity and arrangement: Five petals arranged in a single whorl and fused towards the base into an elongated tube; petal lobes not imbricate. Petal lobe length: About 3.2 cm. Petal lobe width: About 2.5 cm. Petal lobe shape: Spatulate, asymmetrical. Petal lobe apex: Acuminate. Petal lobe margin: Entire; slightly undulate; not recurved. Petal lobe texture and luster, upper and lower surfaces: Smooth, glabrous; velvety; matte. Throat texture: Smooth, glabrous. Tube texture: Smooth, glabrous. Color: Petal lobe, when opening, upper surface: Close to 10C. Petal lobe, when opening, lower surface: Close to 11B. Petal lobe, fully opened, upper surface: Close to 10C tinged with close to 35D; venation, similar to lamina; color does not change with subsequent development. Petal lobe, fully opened, lower surface: Close to 11B tinged with close to 35B; venation, similar to lamina; color does not change with subsequent development. Throat: Proximally, close to 17B and distally, close to 17B tinged with close to N25B. Tube: Close to 13C and distally, close to N144A.

*Calyx.*—Quantity and arrangement: Five sepals arranged in a single whorl, fused at the base; calyx, star-shaped. Sepal length: About 3.7 mm. Sepal width: About 1.9 mm. Sepal shape: Lanceolate. Sepal apex: Acute. Sepal margin: Entire. Sepal texture, upper and lower surfaces: Smooth, glabrous. Sepal color, upper surface: Close to 144A; towards the apex, close to 60B. Sepal color, lower surface: Proximally, close to 144B and distally, close to 144C variably tinged with close to 60B.

*Peduncles.*—Length: About 3 cm. Diameter: About 2 mm. Texture: Smooth, glabrous. Aspect: Mostly upright to outwardly. Color: Close to 137B.

*Pedicels.*—Length: About 1 cm. Diameter: About 1.9 mm. Texture: Smooth, glabrous. Aspect: Upright to outwardly. Color: Close to 142A variably tinged with close to 63A.

*Reproductive organs.*—Stamens: Quantity and arrangement: Typically five; filaments fused to corolla; anthers, connivent. Anther size: About 1.7 mm by 7.8 mm. Anther shape: Lanceolate. Anther color: Close to 13A. Pollen amount: If present, sparse. Pistils: Quantity: Typically one. Pistil length: About 1.9 cm. Style color: Close to 145D. Stigma shape: Conical. Stigma color: Close to 144B. Ovary color: Close to 145A.

*Seeds and fruits.*—To date, seed and fruit production have not been observed on plants of the new *Mandevilla.*

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 0931' as illustrated and described.

* * * * *